United States Patent
Dalko

(10) Patent No.: US 10,098,827 B2
(45) Date of Patent: Oct. 16, 2018

(54) COMPOUNDS IN THE FAMILY OF N-ACYLAMINO-AMIDES, COMPOSITIONS COMPRISING THEM, AND USES

(71) Applicant: L'OREAL, Paris (FR)

(72) Inventor: Maria Dalko, Versailles (FR)

(73) Assignee: L'OREAL, Paris (FR)

( * ) Notice: Subject to any disclaimer, the term of this patent is extended or adjusted under 35 U.S.C. 154(b) by 0 days.

(21) Appl. No.: 15/536,362

(22) PCT Filed: Dec. 15, 2015

(86) PCT No.: PCT/EP2015/079725
§ 371 (c)(1),
(2) Date: Jun. 15, 2017

(87) PCT Pub. No.: WO2016/096804
PCT Pub. Date: Jun. 23, 2016

(65) Prior Publication Data
US 2017/0360667 A1    Dec. 21, 2017

(30) Foreign Application Priority Data
Dec. 18, 2014  (FR) ...................... 14 62727

(51) Int. Cl.
| A61K 38/00 | (2006.01) |
| A61K 8/44 | (2006.01) |
| A61K 8/64 | (2006.01) |
| C07K 5/062 | (2006.01) |
| A61Q 19/08 | (2006.01) |

(52) U.S. Cl.
CPC .............. *A61K 8/44* (2013.01); *A61K 8/64* (2013.01); *A61Q 19/08* (2013.01); *C07K 5/06026* (2013.01); *A61K 2800/782* (2013.01)

(58) Field of Classification Search
None
See application file for complete search history.

(56) References Cited

FOREIGN PATENT DOCUMENTS

| WO | WO-01/94381 A2 | 12/2001 |
| WO | WO-03/000209 A1 | 1/2003 |

*Primary Examiner* — Jeanette M Lieb
(74) *Attorney, Agent, or Firm* — Polsinelli PC

(57) ABSTRACT

The present application relates to new compounds in the family of N-acylamino-amides having formula (I), compositions, in particular cosmetic compositions comprising them, and their use to treat the signs of aging of skin of the body or face, whether chronobiological or photo-induced, and in particular aging generated by reduced skin elasticity.

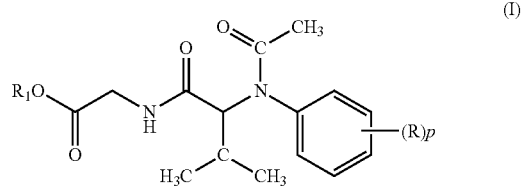

in which
p=1, 2 or 3
R independently denotes a cyano (—CN), hydroxy (—OH), $CO_2R'$ group in which R' denotes a hydrogen atom or linear or branched $C_1$-$C_6$ alkyl group,
$R_1$ denotes a hydrogen atom or a linear or branched $C_1$-$C_6$ alkyl group,
and also the salts and/or isomers and/or solvates thereof.

20 Claims, No Drawings

COMPOUNDS IN THE FAMILY OF N-ACYLAMINO-AMIDES, COMPOSITIONS COMPRISING THEM, AND USES

CROSS REFERENCE TO RELATED APPLICATIONS

This application is a National Phase filing under 35 U.S.C. § 371 of PCT/EP2015/079725 filed on Dec. 15, 2015; and this application claims priority to Application No. 1462727 filed in France on Dec. 18, 2014 under 35 U.S.C. § 119. The entire contents of each application are hereby incorporated by reference.

The present invention relates to new compounds in the N-acylamino-amide family, to their use in particular in cosmetics, and to compositions, particularly cosmetic compositions which comprise them.

The skin consists of two compartments, a surface compartment, the epidermis, and the other deeper compartment, the dermis, which interact. Natural human epidermis is composed mainly of three types of cells, namely keratinocytes, which form the vast majority, melanocytes and Langerhans cells. Each of these three types of cells contributes, by virtue of their intrinsic functions, to the essential role played in the body by the skin, especially the role of protecting the body against external attacking factors, which is known as the "barrier function".

The epidermis is conventionally divided into a basal layer of keratinocytes that constitutes the germinative layer of the epidermis, a spinous layer consisting of several layers of polyhedral cells positioned on the germinative layers, one to three "granular" layers consisting of flattened cells containing distinct cytoplasmic inclusions, keratohyalin granules, and finally the cornified layer (or stratum corneum), consisting of a set of layers of keratinocytes at the terminal stage of their differentiation, known as corneocytes. Corneocytes are anuclear cells mainly consisting of a fibrous material containing cytokeratins, surrounded by a cornified envelope.

The dermis provides the epidermis with a solid support. It is also its nourishing element. It consists mainly of fibroblasts and of an extracellular matrix predominantly composed of collagen, elastin and a substance, known as ground substance, comprising glycosaminoglycans that are sulfated (e.g. chondroitin sulfate) or not (e.g. hyaluronic acid), proteoglycans and various proteases. These components are synthesized by the fibroblasts. Leukocytes, mast cells or else tissue macrophages are also found therein. Finally, blood vessels and nerve fibers pass through the dermis. The cohesion between the epidermis and the dermis is provided by the dermo-epidermal junction.

It is known that during superficial skin stress, which can in particular be of chemical, physical or bacterial origin, keratinocytes in the outer epidermal layers release biological mediators that can attract certain cells that infiltrate skin, which are themselves responsible for localized transient irritation.

Among biological mediators that can be produced by keratinocytes stressed in this way, mention may be made of chemokines, which are chemoattractant cytokines responsible for recruiting leukocytes to inflammatory sites, including interleukin 8 (IL-8), which is particularly responsible for recruiting neutrophils.

These cells that infiltrate irritated or attacked areas then release enzymes among which mention may be made of leukocyte elastase.

Under the action of this enzyme in particular, extracellular elastic support fibres in the conjunctive tissue may be degraded, thereby reducing skin elasticity.

It is even known that in synergy with cathepsin G, leukocyte elastase can dissociate the entire epidermis by widening interkeratinocyte intercellular spaces. Accordingly, in the long term, the sum of superficial skin microstresses, for example generated by prolonged exposure to UV or by irritants, may cause loss of the skin's natural elasticity with varying degrees of acceleration. The network formed by the elastic fibres in the underlying conjunctive tissue and extracellular spaces may then progressively lose structure. Accelerated skin aging follows (wrinkled and/or less supple skin) by the dermal elastic network changing, and wrinkles being accentuated (deeper wrinkles).

We also know that dermal solidity is mainly ensured by collagen fibers. These fibres consist of fibrils sealed to one another, thus forming more than ten types of different structures. The solidity of the dermis is in large part due to the entanglement of the collagen fibres packed together in all directions. The collagen fibres contribute to the elasticity and tone of the skin and/or the mucous membranes.

The collagen fibres are constantly renewed, but this renewal decreases with age, which leads to thinning of the dermis. This thinning of the dermis is also due to pathological causes, for instance hypersecretion of corticoid hormones, certain pathological conditions, or else vitamin deficiencies (the case of vitamin C in scurvy). It is also accepted that extrinsic factors such as ultraviolet radiation, smoking or certain treatments (glucocorticoids, vitamin D and derivatives, for example) also have an effect on the skin and on its collagen content.

Although they are very strong, collagen fibres are sensitive to certain enzymes known as collagenases. Collagen fibre degradation leads to the appearance of flaccid and wrinkled skin which human beings, preferring the appearance of smooth and taut skin, have always sought to combat.

Moreover, at the menopause, the main changes concerning the dermis are a decrease in collagen content and in the thickness of the dermis. In the case of menopausal women, this results in thinning of the skin and/or the mucous membranes. Women then experience a sensation of "dry skin" or taut skin, and an accentuation of the surface wrinkles and fine lines is observed. The skin has a rough aspect to the touch on palpation. Finally, the skin exhibits reduced suppleness.

The present invention relates to proposing a solution to these various problems, and in particular to proposing new compounds that can be used in cosmetics to limit skin aging, whether it is chronobiological or photo-induced, and particularly aging generated by reduced skin elasticity and/or by collagen degradation in the tissue structure.

Without being held to the present explanation, it can be considered that the fact of bringing compounds that can slow degradation activity in elastic fibres in intercellular spaces to the keratinocytes in the superficial layers of the skin may reduce this accelerated skin aging process due to superficial skin stresses.

Some compounds belonging to the family of N-acylamino-amides are known in the prior art. An example that may be mentioned is document *J. Am. Chem. Soc.*, 1977, 99(18) pp. 6075-82) which describes a synthesis process for the following derivatives:

$N^\alpha$-Acetylglycyl-$N^\alpha$-(benzyl)-DL-valylglycine tert-butyl ester;

$N^\alpha$-Acetylglycyl-$N^\alpha$-(2-nitrobenzyl)-DL-valylglycine tert-butyl ester;

N$^\alpha$-Acetylglycyl-N$^\alpha$-(2,4-dimethyloxybenzyl)-DL-valyl-glycine tert-butyl ester.

Mention may also be made of N-acylamino-amides as described in application FR2810033; these derivatives being capable of being used in cosmetics to limit skin aging, whether chronobiological or photo-induced.

The Applicant has observed that the compounds according to the present invention present clearly superior activity to those compounds described in the prior art.

Therefore the present invention relates to a compound having formula (I) as defined hereinafter, and its salts, isomers and/or solvates.

The invention also relates to a composition, in particular a cosmetic composition comprising at least one compound having formula (I).

The invention also relates to the use of at least one compound having formula (I) or to a composition, in particular a cosmetic composition, comprising said formula to treat the signs of aging of skin of the body or face, whether chronobiological or photo-induced, and in particular aging generated by reduced skin elasticity and/or by collagen degrading in the tissue structure.

The invention also relates to the use of at least one compound having formula (I) or to a composition, in particular a cosmetic composition, comprising said formula to treat wrinkles and/or fine lines, wizened skin, lack of skin elasticity and/or tone, dermal thinning, degradation of collagen fibres, flaccid skin, thinned skin and/or any internal degradation of the skin caused by exposure to ultraviolet radiation.

The invention also relates to the cosmetic use of at least one compound having formula (I) or of a composition, in particular a cosmetic composition, comprising said formula to inhibit elastase activity and/or to limit and/or combat degradation of elastic fibers.

The invention also relates to a method of cosmetic treatment for the skin of the body or face, including the scalp, in which a cosmetic composition as defined hereinafter is applied.

It has in fact been observed that compounds having formula (I) presented esterase inhibition activity and that they could therefore be used to limit and/or combat degradation in elastic fibers.

Another subject of the present invention is the use of at least one compound having formula (I) to treat the cutaneous signs of aging.

"Signs of skin aging" means any change in the external appearance due to aging, whether it be chronobiological and/or photo-induced aging, for instance wrinkles and fine lines, wizened skin, lack of elasticity and/or tone of the skin, dermal thinning and/or collagen fiber degradation which causes the skin to appear flaccid and wrinkled, but also any internal modification of the skin that is not automatically reflected by a modified outer appearance, for instance any internal degradation of the skin, particularly of elastin fibers, or elastic fibers, caused by exposure to ultraviolet radiation.

A benefit of the present invention lies in the fact that compounds having formula (I) may be easily prepared.

The compounds that can be used in the present invention therefore correspond to formula (I) below, and to its salts and/or isomers and/or solvates thereof:

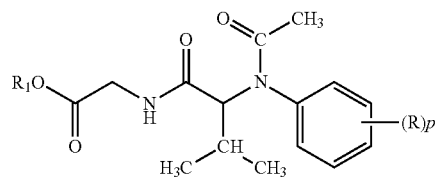

in which p=1, 2 or 3

R independently denotes a cyano (—CN), hydroxy (—OH), $CO_2R'$ group in which R' denotes a hydrogen atom or linear or branched $C_1$-$C_6$ alkyl group $R_1$ denotes a hydrogen atom or a linear or branched $C_1$-$C_6$ alkyl group.

For the purpose of the present invention, the term "salts" is intended to mean organic or inorganic salts.

Among inorganic salts mention may be made of alkali metal salts, alkaline earth metal salts, and transition metal salts.

Among organic salts, mention may be made of amine salts such as triethanolamine salts or the salts of L- or D-amino acids such as lysine or arginine salts, quaternary ammoniums.

Optical isomers are also included in this definition of compounds having formula (I), in isolated forms or as racemic mixtures.

The compound having formula (I) may also be in the form of solvates, for example a hydrate or a solvate of a linear or branched alcohol such as ethanol or isopropanol.

Linear or branched $C_1$-$C_6$ alkyl group is understood in particular to mean methyl, ethyl, n-propyl, n-butyl, n-pentyl, n-hexyl, isopropyl, tert-butyl, iso-butyl-groups.

According to one variant, p=1 or 2 and R independently denotes a cyano (—CN), hydroxy (—OH), $CO_2R'$ group in which R' denotes a hydrogen atom or linear or branched $C_1$-$C_4$ alkyl group, preferably linear.

According to another variant, $R_1$ denotes a hydrogen atom or a linear or branched $C_1$-$C_6$ alkyl group, preferably a hydrogen atom or a linear or branched $C_1$-$C_4$ alkyl group, particularly a linear group. Preferably, $R_1$ denotes a hydrogen atom.

According to another variant, p=1 or 2, R independently denotes a cyano (—CN), hydroxy (—OH), $CO_2R'$ group in which R' denotes a hydrogen atom or a linear or branched $C_1$-$C_4$ alkyl group, preferably linear, and $R_1$ denotes a hydrogen atom.

Among the particularly preferred compounds, mention may be made of the following compounds (a) to (h) and the salts, optical isomers and/or solvates thereof:

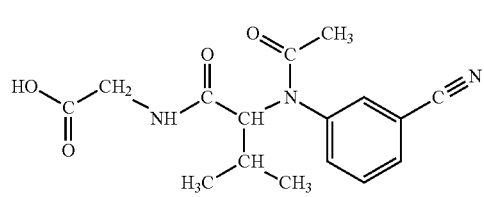

-continued (b) 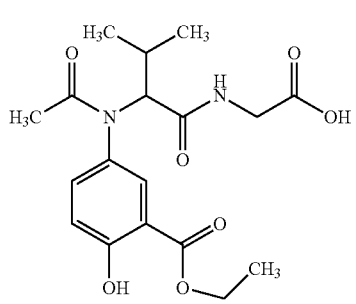

(c) 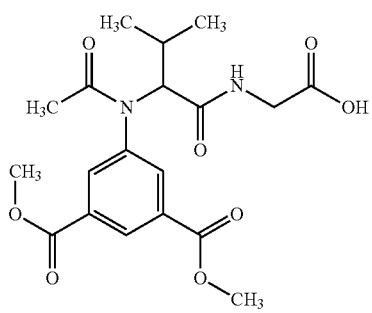 [SMILES: COC(=O)c1cc(C(=O)OC)cc(N(C(C)=O)C(C(=O)NCC(=O)O)C(C)C)c1]

(d) 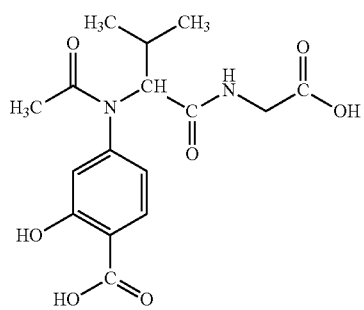

(e) 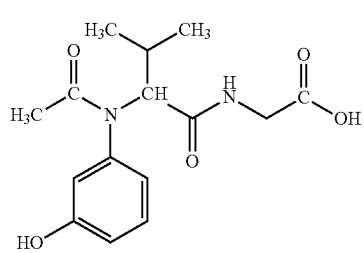

(f) 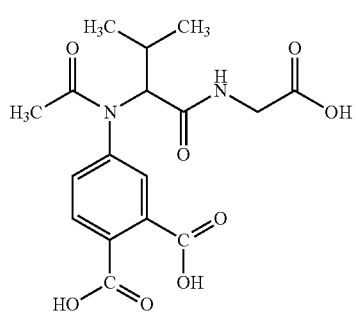 [SMILES: CC(=O)N(c1ccc(C(=O)O)c(C(=O)O)c1)C(C(=O)NCC(=O)O)C(C)C]

-continued (g) 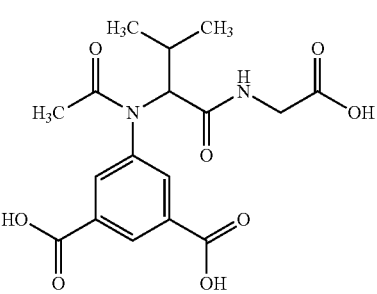 [SMILES: CC(=O)N(c1cc(C(=O)O)cc(C(=O)O)c1)C(C(=O)NCC(=O)O)C(C)C]

(h) 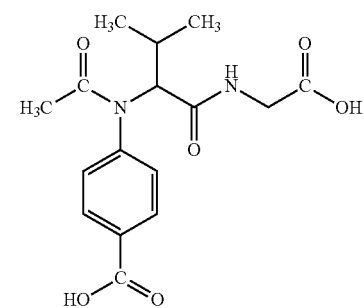 [SMILES: CC(=O)N(c1ccc(C(=O)O)cc1)C(C(=O)NCC(=O)O)C(C)C]

Compound (a) and its salts, optical isomers, and/or solvates are most particularly preferred.

The compounds according to the invention may be readily prepared by a person skilled in the art on the basis of his general knowledge. In particular a carboxylic acid, an aldehyde, a compound with an amine function and an isonitrile can be reacted together, according to the Ugi reaction described in the literature for example in Ugi, I; Meyr, R.; Fetzer, U.; Steinbrückner, C. (1959). "Versuche mit Isonitrilen". *Angew. Chem.* 71 (11): 386.

Accordingly, compounds having formula (I) may be obtained by reaction between an aniline, a carboxylic acid, an aldehyde in a protic solvent such as methanol, then by adding an isonitrile. The reaction medium is held with stirring between 10 and 25° C. for 2 to 24 h.

At the end of the reaction, the reaction medium is purified.

The ester functions of compounds (I) obtained by the Ugi reaction may be saponified by known saponification methods, for example in methanol by using an aqueous solution of strong base such as LiOH at 10%.

Of course, during the synthesis of compounds according to the invention, and depending on the nature of the different groups present in the starting compounds, the person skilled in the art can take care to protect some substituents so that they do not interact in the remainder of the reactions.

The quantity of compound to be used in the compositions according to the invention may be easily determined by the person skilled in the art, depending on the nature of the compound used, the person to be treated and/or the desired effect. Generally, this quantity may be comprised between 0.00001 and 20% by weight relative to the total weight of the composition, in particular between 0.001 and 10% by weight, and preferably between 0.05 and 5% by weight, more preferably between 0.1 and 3% by weight, and most preferably between 0.5 and 2% by weight.

The compounds having formula (I) may in particular be employed, alone or in mixtures, in a composition that comprises a physiologically acceptable medium, in particular in a cosmetic composition that comprises therefore moreover a cosmetically acceptable medium.

In the scope of the invention, and unless otherwise stated, the term "physiologically acceptable medium" is understood to mean a medium that is suitable for the topical administration of a composition. A physiologically acceptable medium is preferentially a cosmetically acceptable medium, i.e. a medium that has no unpleasant odour or appearance, and that is entirely compatible with the topical administration route. In the case where the composition is intended for topical administration, i.e. by application at the surface of the keratin material under consideration, such a medium is considered in particular to be physiologically acceptable when it does not cause discomfort during application that is unacceptable to the user.

The physiologically acceptable medium is generally adapted to the nature of the support onto which the composition has to be applied, and to the appearance under which the composition must be packaged.

The physiologically acceptable medium in which the compounds according to the invention can be used, and also its constituents, their amount, the pharmaceutical delivery form of the composition and the preparation method thereof may be chosen by those skilled in the art on the basis of their general knowledge as a function of the type of composition desired.

Generally speaking, this medium may be anhydrous or aqueous. It may thus comprise an aqueous phase and/or an oil phase.

For topical application to the skin, the composition may be in the form in particular of an aqueous or oily solution or of a dispersion of the lotion or serum type, of emulsions of liquid or semi-liquid consistency of the milk type, obtained by dispersion of an oil phase in an aqueous phase (O/W), or vice versa (W/O), or of suspensions or emulsions of soft consistency, of the aqueous or anhydrous gel or cream type, or else of microcapsules or microparticles, or of vesicular dispersions of ionic and/or nonionic type.

For application to the hair, the composition may be in the form of aqueous, alcoholic or aqueous-alcoholic solutions; in the form of creams, gels, emulsions or mousses; in the form of aerosol compositions also comprising a propellant under pressure.

When the composition is in aqueous form, especially in the form of an aqueous dispersion, emulsion or solution, it may comprise an aqueous phase, which may comprise water, a floral water and/or a mineral water.

Said aqueous phase may further comprise alcohols such as $C_2$-$C_6$ monoalcohols and/or polyols such as glycerol, butyleneglycol, isoprene glycol, propylene glycol, polyethylene glycols, dipropylene glycol, hexylene glycol, pentylene glycol and their mixtures.

When the composition according to the invention is in the form of an emulsion, it may optionally further comprise a surfactant, preferably in a quantity from 0.01 to 30% by weight relative to the total weight of the composition.

The composition according to the invention may also comprise an oil phase, in particular constituted of fatty substances that are liquid at 25° C., such as oils of animal, vegetable, mineral or synthetic origin, volatile or not; fatty substances solid at 25° C. such as waxes of animal, vegetable, mineral or synthetic origin; pasty fats; gums; and their mixtures.

The volatile oils are generally oils having, at 25° C., a saturating vapor tension at least equal to 0.5 millibar (i.e. 50 Pa).

Among oil phase constituent parts, mention may be made of:

volatile cyclic silicones having from 3 to 8 and preferably 4 to 6 silicon atoms.

cyclocopolymers of the dimethylsiloxane/methylalkylsiloxane type.

volatile linear silicones having from 2 to 9 silicon atoms. volatile hydrocarbon-based oils, such as isoparaffins and in particular isododecane and fluorinated oils.

poly($C_1$-$C_{20}$)alkyl siloxanes and in particular those with terminal trimethylsilyl substituents, among which mention may be made of linear polydimethylsiloxanes and alkylmethylpolysiloxanes such as cetyldimethicone (CTFA name), silicones modified by aliphatic and/or aromatic groups, optionally fluorinated, or functional groups such as hydroxyl, thiol and/or amine groups.

phenylated silicone oils.

oils of animal, vegetable or mineral origin, and in particular animal or vegetable oils formed by fatty acid esters and polyol esters, in particular liquid triglycerides, for example sunflower oil, corn oil, soybean oil, marrow oil, grapeseed oil, sesame oil, hazelnut oil, apricot oil, almond oil or avocado oil; fish oils, glyceryl tricaprocaprylate, or vegetable or animal oils having formula $R_1COOR_2$ in which $R_1$ represents a higher fatty acid residue comprising from 7 to 19 carbon atoms and $R_2$ represents a branched hydrocarbon-based chain containing from 3 to 20 carbon atoms, for example purcellin oil; liquid paraffin, petroleum jelly, perhydrosqualene, wheatgerm oil, beauty-leaf oil, sesame oil, macadamia oil, grapeseed oil, rapeseed oil, coconut oil, peanut oil, palm oil, castor oil, jojoba oil, olive oil, cereal germ oil; fatty acid esters; alcohols; acetylglycerides; octanoates, decanoates or ricinoleates or polyalcohols; fatty acid triglycerides; glycerides;

fluoro and perfluorinated oils;

silicone gums;

waxes of animal, vegetable, mineral or synthetic origin such as microcrystalline waxes, paraffin wax, petroleum jelly wax, ozokerites, montan waxes, beeswax, lanolin and its derivatives; candelilla wax, ouricurry wax, carnauba wax, Japan wax, cocoa butter, cork fiber wax or sugar cane wax, hydrogenated oils that are solid at 25° C., ozokerites, fatty esters and glycerides that are solid at 25° C.; polyethylene waxes and the waxes obtained by Fischer-Tropsch synthesis; hydrogenated oils that are solid at 25° C.; lanolins; fatty esters that are solid at 25° C.; silicone waxes; fluorinated waxes.

In a known manner, the composition according to the invention may comprise adjuvants that are common in the field under consideration, such as hydrophilic or lipophilic gelling agents, hydrophilic or lipophilic additives, active ingredients in particular hydrophilic or lipophilic cosmetics, preservatives, antioxidants, solvents, fragrances, fillers, pigments, pearlizers, UV filters, odor absorbers and colorants. Depending on their nature, these adjuvants can be introduced into the oil phase, into the aqueous phase and/or into lipid spheres.

The nature and quantity of these adjuvants may be chosen by the person skilled in the art, on the basis of his general knowledge, so as to obtain the desired presentation form for the composition. In any case, a person skilled in the art will take care to select the optional additional compounds and/or the amount thereof such that the advantageous properties of the composition used according to the invention are not, or are not substantially, adversely affected by the envisaged addition.

The cosmetic compositions according to the invention may in particular be presented in the form of a cosmetic composition intended for the care and/or treatment of areas having undergone skin stress or microstress, in particular generated by exposure to UV and/or contact with an irritating product.

Accordingly, the compositions according to the invention may in particular be presented in the form of:

- a care, treatment, cleansing, or protecting product for skin of the body or face including the scalp, such as a care composition (day cream, night cream, moisturizer) for the face or body; an anti-wrinkle or anti-age composition for the face; a mattifying composition for the face; a composition for irritated skin; a make-up removal composition; a body lotion, in particular moisturizing, optionally after-sun care;
- a composition for sun protection, artificial tanning (self-tanning agent) or an after-sun care treatment;
- a haircare composition, and in particular a sun protection cream or gel; a care composition for the scalp, in particular anti-hair loss or for hair regrowth; an anti-parasite shampoo;
- a product for making up the skin of the face, body or lips, such as a foundation, tinted cream, blush or eye shadow, loose or compact powder, concealer stick, cover stick, lipstick, or lip care product;
- an oral hygiene product such as a toothbrush or a mouthwash.

The compositions according to the invention find a preferred application as care composition for the skin of the face, of the anti-wrinkle or anti-age type, and as sun protection or after-sun composition.

The present invention also relates to a method for cosmetic treatment of the skin of the body or face, including the scalp, in which a cosmetic composition comprising an effective quantity of at least one compound having formula (I) is applied, left in contact then optionally rinsed off.

The cosmetic treatment method of the invention may in particular be performed by applying the cosmetic compositions as defined above, according to the usual technique for the use of these compositions. For example: application of creams, gels, sera, lotions, makeup-removing milks or sun protection compositions to the skin or to dry hair, or application of a scalp lotion to wet hair; application of toothpaste to gums.

The invention is illustrated in more detail in the following examples.

EXAMPLE 1: SYNTHESIS OF N-ACETYL-N-(4-CARBOXY-3-HYDROXY-PHENYL)VALYLGLYCINE 1 AND ITS ETHYL DIESTER A

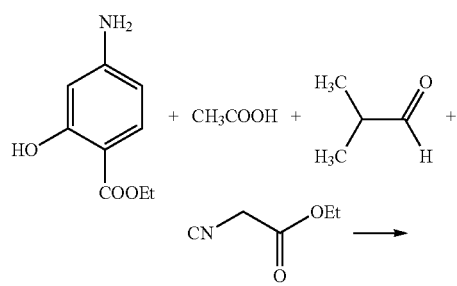

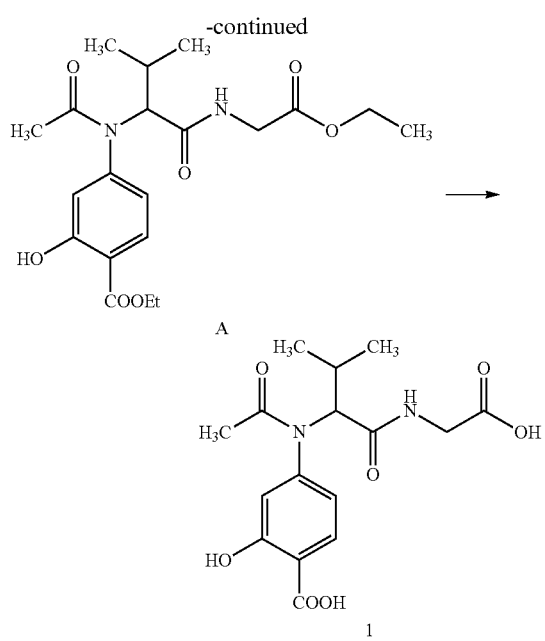

To a stirred solution of ethyl 4-amino-2-hydroxybenzoate (3.62 g, 20 mmol) and glacial acetic acid (1.2 g, 20 mmol) in 60 ml of methanol previously cooled to 10° C. under nitrogen, isobutyraldehyde is added (2.8 g, 40 mmol). After 5 min stirring at 10° C., ethyl isocyanoacetate (2.26 g, 20 mmol) is added dropwise then at the end of the addition, is held with stirring at 10° C. for 2 h then at room temperature for 12 hours. The reaction medium is concentrated under vacuum then purified by chromatography on a silica column twice to produce 1.8 g (Yield 22%) of intermediate A in the form of yellow oil. Intermediate A is purified again by preparative HPLC to produce 800 mg of pure diester A.

To a solution of 0.38 g of diester A (1 mmol) in 10 mL of methanol, 0.96 g (4 mmol) of an aqueous solution of 10% LiOH is added. The medium is held with stirring at room temperature for 15 h then the solvent is removed under vacuum. The resulting aqueous solution is acidified to pH=2 by an aqueous 10% HCl solution, then extracted 3 times by 20 mL of dichloromethane. After drying the combined organic phases on magnesium sulfate and concentrating under vacuum, the crude product is purified by chromatography (2:1 dichloromethane/methanol eluent) to produce 0.158 g of compound 1 in the form of a yellow solid (Yield=45%).

The NMR spectrum matches the expected structure.

EXAMPLE 2: SYNTHESIS OF N-ACETYL-N-(3,4-DICARBOXYPHENYL) VALYLGLYCINE 2 AND ITS TRIETHYL ESTER B

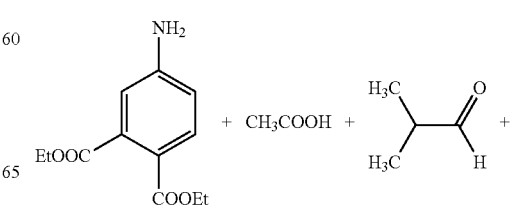

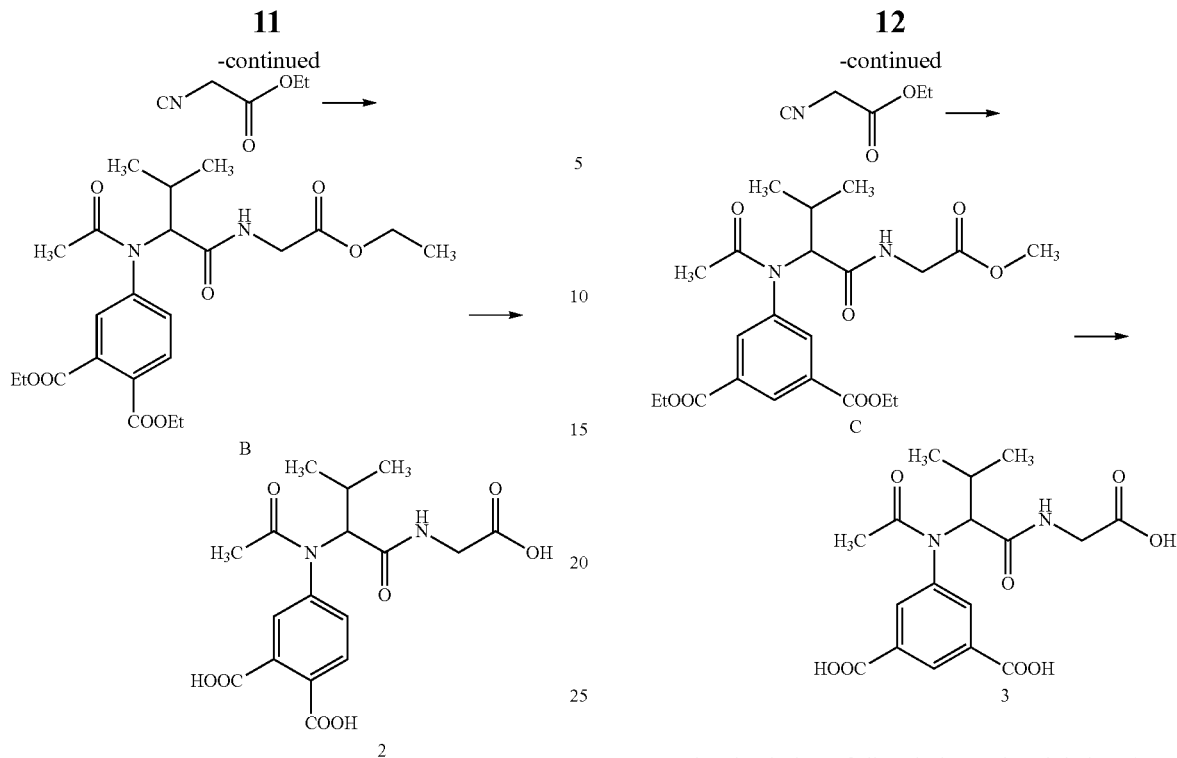

To a stirred solution of dimethyl 4-aminophthalate (1.05 g, 5 mmol) and glacial acetic acid (0.3 g, 5 mmol) in 30 mL of methanol previously cooled to 10° C. under nitrogen, isobutyraldehyde is added (0.72 g, 10 mmol). After 30 min stirring at 10° C., ethyl isocyanoacetate (0.57 g, 5 mmol) is added dropwise then at the end of the addition, is held with stirring at 10° C. for 2 h then at room temperature for 12 hours. The reaction medium is concentrated under vacuum then purified by chromatography on a silica column twice to produce 0.6 g (Yield 27%) of triester B in the form of a pale yellow solid.

To a solution of 2.2 g of diester B (5.05 mmol) in 20 mL of THF, 8.5 g (20.2 mmol) of an aqueous solution of 10% LiOH is added. The medium is held with stirring at room temperature for 15 h then the solvent is removed under vacuum. The resulting aqueous solution is acidified to pH=2 by an aqueous 10% HCl solution, then extracted 3 times by 30 mL of ethyl acetate. After drying the combined organic phases on magnesium sulfate and concentrating under vacuum, the crude product is purified by chromatography to produce 0.28 g of compound 2 in the form of a yellow solid (Yield=14.2%).

The NMR spectrum matches the expected structure.

EXAMPLE 3: SYNTHESIS OF N-ACETYL-N-(3,5-DICARBOXYPHENYL) VALYLGLYCINE 3 AND ITS TRIETHYL ESTER C

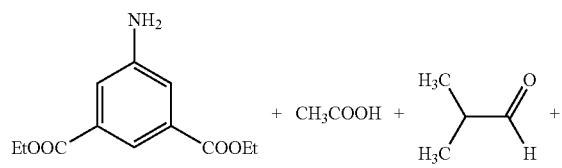

To a stirred solution of dimethyl 5-aminophthalate (2.09 g, 10 mmol) and glacial acetic acid (0.6 g, 10 mmol) in 30 mL of methanol under nitrogen, isobutyraldehyde is added (1.44 g, 20 mmol). The medium is brought to reflux for 30 min, then ethyl isocyanoacetate is added dropwise (1.13 g, 10 mmol). After addition, the medium is held at reflux for 4 h then cooled and concentrated under vacuum before being purified by column chromatography on silica to produce 1.89 g (Yield 43%) of triester C in the form of a white solid.

To a solution of 1.31 g of triester C (3 mmol) in 30 mL of methanol, 0.504 g (12 mmol) of LiOH is added. The medium is held with stirring at room temperature for 15 h then the solvent is removed under vacuum. The residue was poured into 30 mL of water, acidified to pH=2 by an aqueous 10% HCl solution, then left at 5° C. for 4 days. The crystals formed were filtered and dried to produce 0.8 g of compound 3 in the form of white crystals (yield=70%).

The NMR spectrum matches the expected structure.

EXAMPLE 4: SYNTHESIS OF N-ACETYL-N-(3-HYDROXYPHENYL) VALYLGLYCINE 4 AND ITS ETHYL ESTER D

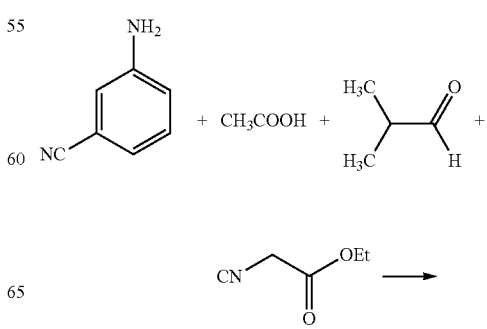

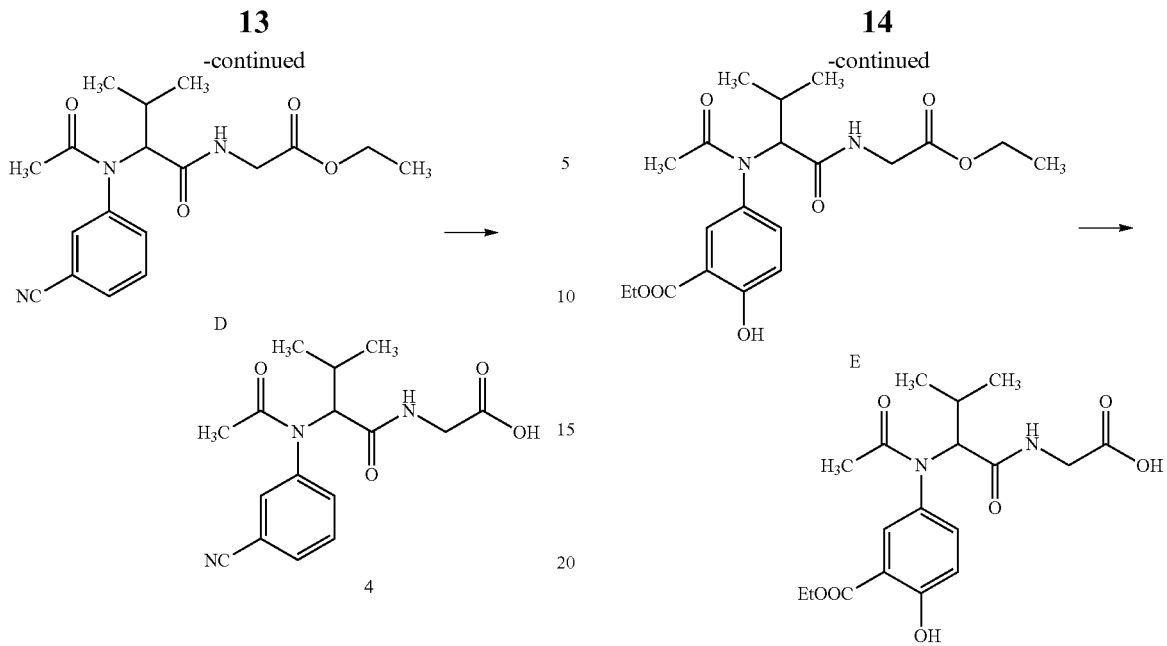

In a reactor, 1.05 eq of 3-amino-benzonitrile (10 g, 84.65 mmoles) is solubilized in 40 mL of methanol. 1.05 eq of acetic acid (5.079 g, 84.65 mmoles) is added, then the mixture is brought to reflux. As soon as reflux is reached, 2 eq of isobutyraldehyde (12.2 g, 169.3 mmoles) is added and left to react for 30 min at reflux. Next 1 eq ethyl isocyanoacetate (9.25 g, 80.32 mmoles) is added and the mixture is left to react again for 3 h at reflux.

The reaction medium is then concentrated under vacuum and purified on a silica column (dichloromethane/methanol eluent), to produce 15 g of ester D (yield=50%).

The $^1$H and $^{13}$C NMR spectra and the mass spectrum are in accordance with the expected structure of the product D.

Ester D (5 g, 14.48 mmoles) is solubilized in 50 mL of methanol then 2 eq (1.16 g, 29 mmoles) of 1 N aqueous sodium hydroxide solution is added. The mixture is left with stirring for 1 h at room temperature then acidified to pH=2 by an aqueous 1 N HCl solution and the resulting product is purified on a silica column (dichloromethane/methanol eluent). 3.2 g (yield=70%) of compound 4 is produced.

The $^1$H and $^{13}$C NMR spectra and the mass spectrum are in accordance with the expected product 4.

EXAMPLE 5: SYNTHESIS OF N-ACETYL-N-[3-(ETHOXYCARBONYL)-4-HYDROXYPHENYL] VALYLGLYCINE 5 AND ITS ETHYL DIESTER E

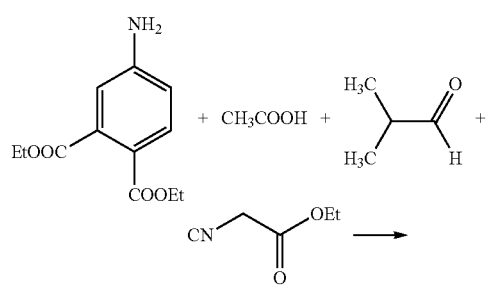

To a solution of 5-ethylaminosalicylate (1.8 g, 10 mmoles) and glacial acetic acid (0.6 g, 10 mmoles) in 30 mL of methanol, isobutyraldehyde is added (1.44 g, 20 mmoles) at 10° C. and under nitrogen.

After 10 min stirring, ethyl isocyanoacetate (1.13 g, 10 mmoles) is added dropwise. The reaction medium is then stirred for 2 h at 10° C., then 12 h at room temperature before being concentrated under vacuum and purified on a silica column (dichloromethane/methanol eluent) to produce diester E (1.4 g, yield=35%).

The $^1$H and $^{13}$C NMR spectra and the mass spectrum are in accordance with the expected structure of the product E.

Diester E (0.72 g, 1.8 mmoles) is saponified in 10 mL of methanol in the presence of LiOH (0.3 g, 7.2 mmoles) for 12 h. The reaction medium is concentrated under vacuum, acidified to pH=2 by a 10% aqueous HCl solution, extracted by 3×30 mL dichloromethane and purified on a silica column (dichloromethane/methanol eluent). 300 mg (50% yield) of compound 5 is thus obtained in the form of a pale yellow solid.

The $^1$H and $^{13}$C NMR and the mass spectrum are in accordance with the expected structure of the product 5.

EXAMPLE 6: SYNTHESIS OF N-ACETYL-N-[3, 5-BIS(METHOXYCARBOXY)PHENYL]VALYL-GLYCINE 6 AND ITS TRIESTER F

To a solution of dimethyl 5-aminoisophthalate (10 g, 47.8 mmoles) and glacial acetic acid (2.87 g, 47.8 mmoles) in 100 mL of methanol, isobutyraldehyde is added (6.89 g, 95.6 mmoles) at 10° C. and under nitrogen.

After 10 min stirring, tert-butyl isocyanoacetate (6.84 g, 47.8 mmoles) is added dropwise. The reaction medium is then held with stirring for 2 h at 10° C., then 96 h at room temperature before being concentrated under vacuum and purified on a silica column (dichloromethane/methanol eluent) to produce 8.65 g of ester F.

The $^1$H and $^{13}$C NMR spectra and the mass spectrum are in accordance with the expected structure of the product F.

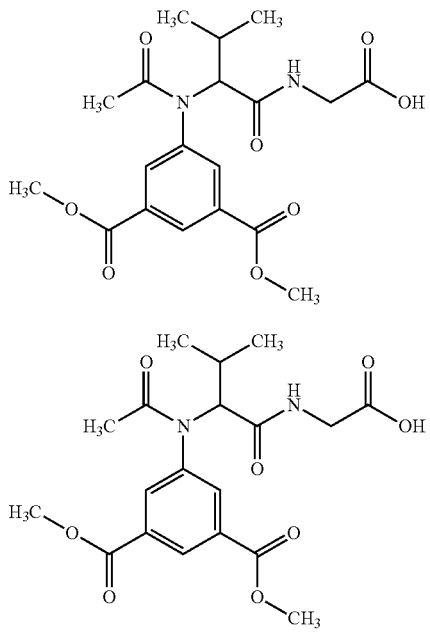

Compound F (2.32 g, 5 mmoles) is saponified in 20 mL of toluene with TsOH.H$_2$O (7.6 g, 18.9 mmole). After 16 h of reaction at room temperature, the medium is concentrated under vacuum then purified on a silica column (dichloromethane/methanol eluent) to produce 306 mg (yield=15%) of compound 6.

The $^1$H and $^{13}$C NMR and the mass spectrum are in accordance with the expected structure of the product 6.

EXAMPLE 7: SYNTHESIS OF N-ACETYL-N-(3-HYDROXYPHENYL) VALYLGLYCINE 7 AND ITS ETHYL ESTER G

To a solution of 3-aminophenol (1.09 g, 10.5 mmoles) and glacial acetic acid (0.63 g, 10.5 mmoles) in 30 mL of methanol, isobutyraldehyde is added (1.44 g, 20 mmoles) at 10° C. and under nitrogen.

After 10 min stirring, ethyl isocyanoacetate (1.13 g, 10 mmoles) is added dropwise then the reaction medium is held with stirring for 2 h at 10° C., then 12 h at room temperature.

The reaction medium is then concentrated under vacuum then purified on a silica column (dichloromethane/methanol eluent), to produce 2.3 g of intermediate ester G (yield=65%).

The $^1$H and $^{13}$C NMR spectra and the mass spectrum are in accordance with the expected structure of the product G.

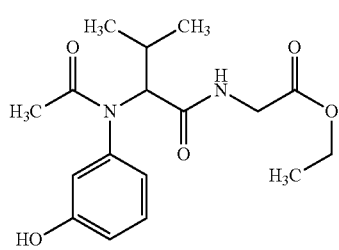

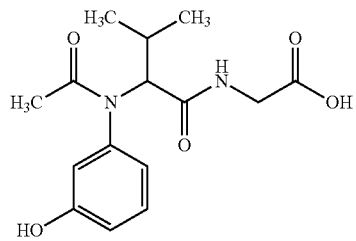

Compound G (0.6 g, 5.4 mmoles) is then saponified in 10 mL of methanol in the presence of LiOH (0.22 g, 5.4 mmoles) in solution in 2 mL of water for 2 h. After acidification at pH=3 by a 5% HCl solution and extractions with 2×20 mL of dichloromethane, the product is purified by chromatography on a silica column (dichloromethane/methanol eluent), to produce 300 mg (yield=50%) of derivative 7.

The $^1$H and $^{13}$C NMR and the mass spectrum are in accordance with the expected structure of the product 7.

EXAMPLE 8: SYNTHESIS OF N-ACETYL-N-(4-HYDROXYPHENYL) VALYLGLYCINE AND ITS DIETHYL ESTER H

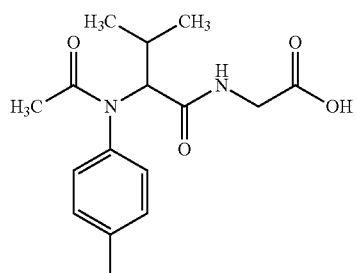

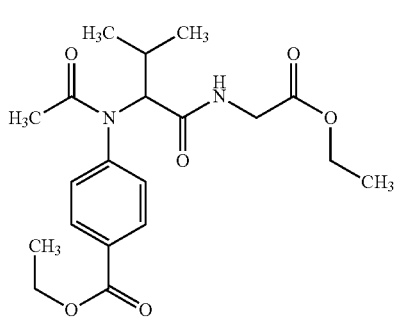

To a solution of 4-ethylaminobenzoate (1.65 g, 10 mmoles) and glacial acetic acid (0.6 g, 10 mmoles) in 30 mL of methanol, isobutyraldehyde is added (1.44 g, 20 mmoles) at 10° C. and under nitrogen. After 10 min stirring, ethyl isocyanoacetate (1.13 g, 10 mmoles) is added dropwise then the stirring is held for 2 h at 10° C., then 12 h at room temperature.

The reaction medium is then concentrated under vacuum and purified on a silica column (dichloromethane/methanol eluent), to produce 1.4 g of intermediate ester H (yield=36%).

The $^1$H and $^{13}$C NMR spectra and the mass spectrum are in accordance with the expected structure of the product H.

Ester H (1 g, 2.5 mmoles) is saponified in 20 mL of ethanol in the presence of 40% aqueous KOH solution for 24 h. After purification on silica column (dichloromethane/methanol eluent), 380 mg (yield=45%) of compound 8 is isolated.

The $^1$H and $^{13}$C NMR spectra and the mass spectrum are in accordance with the expected structure of the product 8.

EXAMPLE 9

The molecules have been evaluated in vitro on a Human Elastase Assay test, available in the CEREP catalog.

The results are expressed as a percentage of activity versus a specific control (activity measured with compounds of the invention/control activity without the compound of the invention)×100.

The control is the enzymatic activity of human leukocyte elastase (HLE) on a reference substrate (MeOSAAPV-pNa at 0.1 mM).

The detection method used is photometry.

This method is described in the literature: Adeyemi et al 1990, J. Pharm. Pharmacol. 42, 487-490.

The results are as follows:

| Test compound | Molecule | Elastase inhibition activity (conc 1 mM) |
|---|---|---|
| Compound 4 (Example 4) | | 35% |
| Compound 5 (Example 5) | | 62% |
| Compound 6 (Example 6) | | 65% |
| Compound 1 (Example 1) | | 98% |
| Compound 7 (Example 7) | | 62% |
| Compound 2 (Example 2) | | 98% |
| Compound 3 (Example 3) | | 98% |
| Compound 8 (Example 8) | | 88% |

EXAMPLE 10

The activity of compound 4 of the invention was compared to that of the compound of the prior art, which differs by the presence of a CF3 group in the place of a CN group.

The concentration that produces 50% inhibition of the human elastase activity (IC50) was measured.

Compound of the invention:

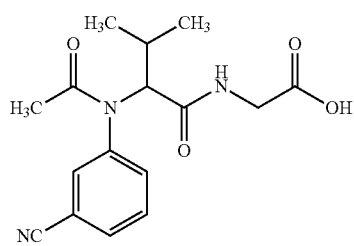
4

Compound outside the invention:

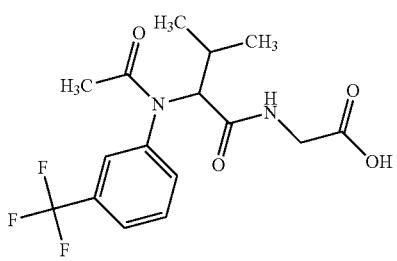
(Z)

Results were as follows:

| Test compound | IC50 |
| --- | --- |
| Compound outside the invention (Z) | 6.38 mM |
| Compound 4 of the invention (Example 4) | 5.6 mM |

Compound 4 is clearly more effective than the compound of the prior art for inhibiting elastase activity.

EXAMPLE 11: COMPOSITION FOR TOPICAL APPLICATION

The following emulsion is prepared conventionally (% by weight):

| | |
| --- | --- |
| compound of example 4 | 1% |
| propylene glycol isostearate | 13% |
| polyethylene glycol (8 OE) | 5% |
| propylene glycol | 3% |
| pentylene glycol | 3% |
| glyceryl stearate and polyethylene glycol stearate (100 OE) | 5% |
| oxyethylenated sorbitan monostearate (20 OE) | 0.5% |
| oxyethylenated (20 OE) and oxypropylenated (5 OP) cetyl alcohol | 1% |
| gellants | 0.5% |
| $C_{12-15}$ alkyl benzoates | 4% |
| ethanol | 3% |
| sodium hydroxide | 0.12% |
| preservatives | qs |
| water | q.s. 100% |

Applied to skin, this composition improves its elasticity.

EXAMPLE 12: FACIAL CARE CREAM

The following oil-in-water emulsion is prepared conventionally (% by weight):

| | |
| --- | --- |
| Compound of example 2 | 1% |
| Glyceryl stearate | 2% |
| Polysorbate 60 (Tween 60 ® sold by the company ICI) | 1% |
| Stearic acid | 1.4% |
| Triethanolamine | 0.7% |
| Carbomer | 0.4% |
| Liquid fraction of shea butter | 12% |
| Perhydrosqualene | 12% |
| Antioxidant | qs |
| Fragrance | qs |
| Preservative | qs |
| Water | q.s. 100% |

EXAMPLE 13: FACIAL LOTION

The following lotion is prepared conventionally (% by weight):

| | |
| --- | --- |
| Liquid petroleum jelly | 7% |
| Compound of example 4 | 1% |
| Glyceryl stearate, polyethylene glycol stearate (100 EO) | 3% |
| Carboxyvinyl polymer | 0.4% |
| Stearyl alcohol | 0.7% |
| Soya extract | 3% |
| NaOH | 0.4% |
| Preservative | qs |
| Water | q.s. 100% |

EXAMPLE 14: HAIR LOTION

The following lotion is prepared conventionally (% by weight):

| | |
| --- | --- |
| compound of example 4 | 1% |
| propylene glycol | 23% |
| ethanol | 55% |
| water | q.s. 100% |

This lotion can be applied to the scalp, to prevent the effects of UV, before and/or after sun exposure.

EXAMPLE 15: ANTI-HAIR LOSS LOTION

The following lotion is prepared conventionally (% by weight):

| | |
| --- | --- |
| compound of example 2 | 1% |
| propylene glycol | 23% |
| ethanol | 55% |
| Aminexil | 1.5% |
| water | q.s. 100% |

This anti-hair loss lotion can be applied to the scalp.

The invention claimed is:

1. A compound having formula (I):

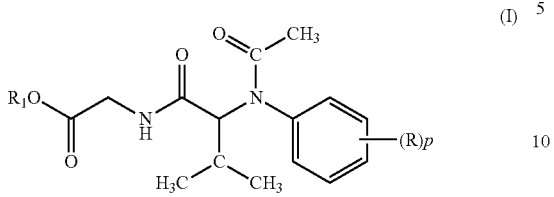

in which p=1, 2 or 3

R independently denotes a cyano (—CN), hydroxy (—OH), CO₂R' group in which R' denotes a hydrogen atom or a linear or branched $C_1$-$C_6$ alkyl group $R_1$ denotes a hydrogen atom or a linear or branched $C_1$-$C_6$ alkyl group, salts thereof, isomers thereof, solvates thereof, and mixtures thereof.

2. The compound as claimed in claim 1, in which:

p=1 or 2 and R independently denotes a cyano (—CN), hydroxy (—OH), CO₂R' group in which R' denotes a hydrogen atom or a linear or branched $C_1$-$C_4$ alkyl group.

3. The compound as claimed in claim 1, in which:

$R_1$ denotes a hydrogen atom or a linear or branched $C_1$-$C_6$ alkyl group.

4. The compound as claimed in claim 1, in which:

p=1 or 2, and R denotes independently a cyano (—CN), hydroxy (—OH), CO₂R' group in which R' denotes a hydrogen atom or a linear or branched $C_1$-$C_4$ alkyl group and $R_1$ denotes a hydrogen atom.

5. The compound as claimed in claim 1, in which the compound having formula (I) denotes a compound chosen from the following compounds (a) to (h) salts thereof, optical isomers thereof, and solvates thereof, and mixtures thereof, (a)
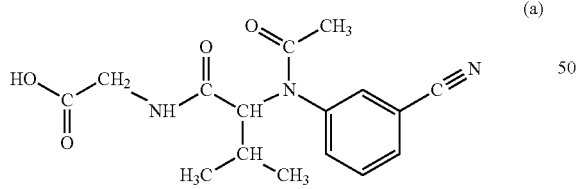

(b)
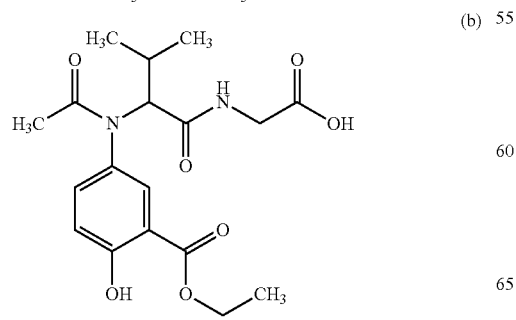

(c)
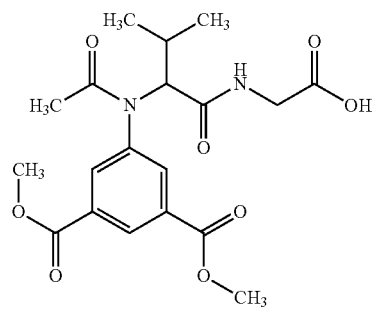

(d)
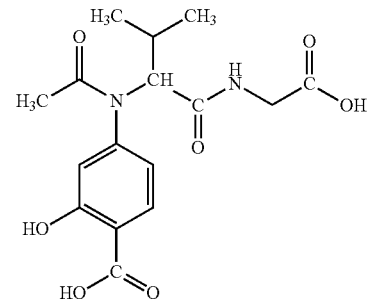

(e)
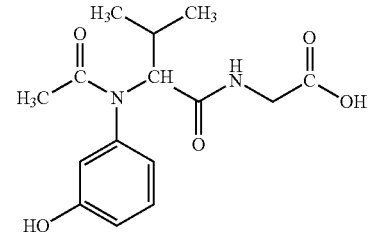

(f)
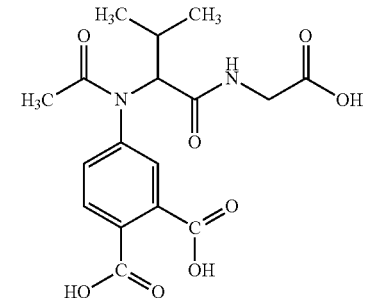

(g)
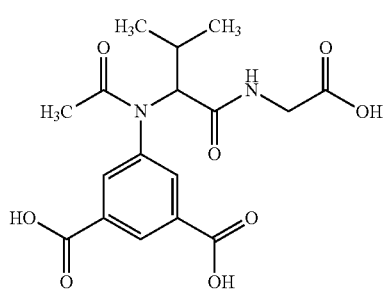

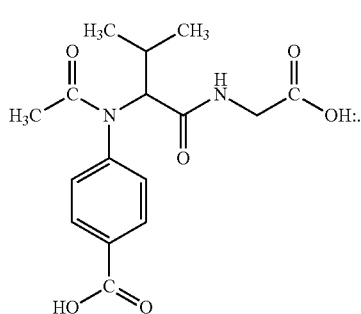
(h)

6. The compound as claimed in claim 1, in which the compound having formula (I) denotes the following compound (a), salts thereof, optical isomers thereof, and solvates thereof, and mixtures thereof:

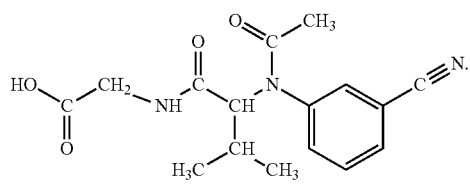
(a)

7. A composition comprising at least one compound having formula (I) as defined in claim 1.

8. A cosmetic composition comprising at least one compound having formula (I) as defined in claim 1.

9. The composition as claimed in claim 7, in which the compound having formula (I) is present in a quantity between 0.00001 and 20% by weight relative to the total weight of the composition.

10. The composition as claimed in claim 7, presented in the form of a cosmetic composition intended for the care and/or treatment of areas having undergone skin stress or microstress.

11. The composition as claimed in claim 7, presented in the form of:

a care, treatment, cleansing, or protecting product for skin of the body or face including the scalp; a mattifying composition for the face; a composition for irritated skin;

a composition for sun protection, artificial tanning (self-tanning agent) or an after-sun care treatment;

a haircare composition; a care composition for the scalp;

a product for making up the skin of the face;

an oral hygiene product.

12. The composition as claimed in claim 7, presented in the form of a care composition for the skin of the face, of an anti-wrinkle or anti-aging composition, or a sun protection or after-sun composition.

13. A method of cosmetic treatment of signs of aging of skin of the body or face which comprises applying to said skin at least one compound having formula (I) as defined in claim 1 or a composition comprising said compound.

14. A method of cosmetic treatment of skin to reduce wrinkles and/or fine lines, wizened skin, lack of skin elasticity and/or tone, dermal thinning, degradation of collagen fibers, flaccid skin, thinned skin; internal degradation of the skin caused by exposure to ultraviolet radiation which comprises applying to said skin at least one compound having formula (I) according to claim 1 or a composition comprising said compound.

15. A method of cosmetic treatment of skin to inhibit the activity of elastases and/or to limit and/or combat degradation of elastic fibers which comprises applying to said skin at least one compound having formula (I) according to claim 1 or a composition comprising said compound.

16. A method of cosmetic treatment for the scalp to reduce hair loss, promote hair regrowth, or prevent the effects of UV, which comprises applying to said scalp at least one compound having formula (I) according to claim 1 or a cosmetic composition comprising said compound.

17. The compound as claimed in claim 2, in which:

$R_1$ denotes a hydrogen atom or a linear or branched $C_1$-$C_6$ alkyl group.

18. A composition comprising at least one compound having formula (I) as defined in claim 2.

19. A composition comprising at least one compound having formula (I) as defined in claim 3.

20. A composition comprising at least one compound having formula (I) as defined in claim 4.

* * * * *